(12) United States Patent
Goomer

(10) Patent No.: US 6,573,101 B1
(45) Date of Patent: *Jun. 3, 2003

(54) COMPOSITIONS FOR RECEPTOR/ LIPOSOME MEDIATED TRANSFECTION AND METHODS OF USING SAME

(75) Inventor: Randal S. Goomer, La Costa, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/248,256

(22) Filed: Feb. 11, 1999

Related U.S. Application Data

(60) Provisional application No. 60/074,468, filed on Feb. 12, 1998.

(51) Int. Cl.$^7$ .............................................. C12N 15/88
(52) U.S. Cl. ...................................... 435/458; 424/450
(58) Field of Search .......................... 514/44; 128/898; 424/450; 435/455, 458

(56) References Cited

U.S. PATENT DOCUMENTS

| | | | | |
|---|---|---|---|---|
| 5,128,257 A | * | 7/1992 | Baer ......................... | 435/173 |
| 5,605,890 A | * | 2/1997 | Agarwal et al. .............. | 514/44 |
| 5,736,392 A | * | 4/1998 | Hawley-Nelson et al. .. | 435/320 |
| 5,776,746 A | * | 7/1998 | Denney, Jr. ............... | 435/172.3 |
| 5,830,730 A | * | 11/1998 | German et al. ........... | 435/172.3 |
| 5,842,477 A | * | 12/1998 | Naughton et al. .......... | 128/898 |
| 6,074,667 A | * | 6/2000 | Kinnunen et al. .......... | 424/450 |

OTHER PUBLICATIONS

Lee et al (1996). J. Biol. Chem 271(14): 8481–8487. See entire document, especially the abstract; Materials and methods: p. 8482, column 1, lines 3 and 4 of first paragraph, and lines 1–6 of second paragraph, and lines 1–6 of fifth paragraph. See also Apr. 1996.*

Kreuzner et al (1996). Atherosclerosis 124(1): 49–60, entire document, see especially abstract, 1996.*

Raja–Walia et al (1995). Gene Therapy 2(8): 521–530. Abstract only, Oct. 1995.*

Chernomordik (Biochim. Biophys. Acta. 1070: 193–197, 1991. See entire document, especially abstract, and p. 194, column 1, lines 5 and 6, 1991.*

Cheng (Human Gene Therapy 7: 275–282, 1996).See entire document, especially lines 2 and 3 of abstract, Feb. 1996.*

Weissmann et al. Trans. Assoc. Am. Phys. 89: 171–183, abstract only, 1976.*

Bolin et al. Scand. J. Gastroent. 16(7): 897–901, abstract only, 1981.*

Hapala (Critical Reviews in Biotechnology 17(2): 105–122, see entire document, especially pp. 108–111, particularly the paragraph bridging pp. 108–109, the first full paragraph on p. 110, and the first full paragraph on p. 111, 1997.*

Voet et al., Biochemistry, Second Edition, New York, John Wiley & Sons, publishers, 1995. See Fig. 23–2 on p. 664.*

Verma et al., Gene therapy—promises, problems and prospects; 1997, Nature vol. 389, 239–242.*

W. Anderson, Human gene therapy; 1998, Nature vol. 392, 25–30.*

S. Orkin; Report and recommendations of the panel to assess the NIH investment in research on gene therapy, Dec. 1995; 1–38.*

You et al.; Surfactant–medicated gene transfer for animals cells, 1997, Cytotechnology 25; 45–52.*

Staedal et al.; High–efficiency transfection of primary human keratinocytes with positively charged lipopolyamine: DNA complexes, 1994, The Society for Investigative Dermatology, vol. 102, No. 5: 768–772.*

Ammitzboli et al. (Acta Neurol. Scand. 53(2): 137–1511976.*

Ohno–Shosaku et. al.(J. Membr. Biol.85(3): 269–280,1985.*

Machy et. al.; Gene transfer from targeted liposomes to specific lymphoid cells by electroporation, 1988, Proc. Natl. Acad. Sci. vol. 85: 8027–8031.*

Boucher; Current status of CF gene therapy, 1996, TIG, vol. 12, NO.3:1–4.*

Boucher, Status of gene therapy for cystic fibrosis lung disease, 1999, Journal of Clinical Investigation, vol. 103, No. 4: 441–445.*

Resenfeld et.al.; Impact of basic research on tomorrow's medicine, 1996, Chest 109: 241–252.*

Klareskog et.al.; Expression of HLA–DR and HLA–DQ antigens on cells within the cartilage–pannus junction in rheumatoid arthritis, 1984, Rheumatol Int. 4: 11–15.*

Zhao et.al.; Amplified Gene Expression in CD59–transfected Chinese Hamster Ovary Cells . . . of Human Complement, 1991, Journal of Biological Chemistry, vol. 266: 13418–13422.*

Trubetsky et.al.; Cationic Liposomes enhance targeted delivery and expression of e xogenous DNA . . . conjugate in mouse lung endothelial cells, 1992, Biochimica et Biophysica Acta 1131: 311–313.*

(List continued on next page.)

Primary Examiner—James Ketter
Assistant Examiner—Richard Schnizer
(74) Attorney, Agent, or Firm—Medlen & Carroll, LLP

(57) ABSTRACT

The present invention relates generally to the delivery of nucleic acid molecules into cells and, more specifically, to compositions and methods for the high efficiency delivery of nucleic acid molecules into cells.

24 Claims, 9 Drawing Sheets

(4 of 9 Drawing Sheet(s) Filed in Color)

OTHER PUBLICATIONS

Straedel et.al.; High–Efficiency Transfection of Primary Human Keratinocytes with Posotively Charged Lipopolyamine: DNA Complexes, 1994, Efficient Transfection of Human Keratinocytes, vol. 102: 768–772. T.*

Prisby, Material Safety Data Sheet, 1997: 1–4.*

Sigma Product Information Sheet; Tergitol NP–40:1–2.*

Rosenecker et.al.; Towards Gene Therapy of Cystic Fibrosis, 1998, European Journal of Medical Research, 149–156.*

Vladimir S. Trubetskoy et al., Bioconjugate Chem. 1992, 3, pp. 323–327.*

Feero et al., "Selection and use of ligands for receptor–mediated gene delivery to myogenic cells," *Gene Therapy* 4:664–674 (1997).

Gao et al., "Potentiation of Cationic Liposome–Mediated Gene Delivery by Polycations," *Biochemistry* 35:1027–1036 (1996).

Trubetskoy et al., "Cationic liposomes enhance targeted delivery and expression of exogenous DNA mediated by N–terminal modified poly (L–lysine)–antibody conjugate in mouse lung endothelial cells," *Biophys* 1131:311–313 (1992).

Wagner, et al., "Transferrin–polycation conjugates as carriers for DNA uptake into cells," *Proc. Natl. Acad. Sci. USA* 87:3410–3414 (1990).

Alton et al., "Non–invasive liposome–mediated gene delivery can correct the ion transport defect in cystic fibrosis mutant mice," *Nature Genet.* 5:135–142 (1993).

Brant et al., "Assessment of liposome–mediated transfectional efficacy of aged human chondroprogenitor cells," *Am. Fed. Med. Res.* Abstract (1997).

Cheng, P., "Receptor ligand–facilitated gene tranfer: enhancement of liposome–mediated gene transfer and expression by transferrin," *Human Gene Ther.* 7:275–282 (1996).

Chu et al., "Articular cartilage repair using allogeneic perichondrocyte–seeded biodegradable porous polylactic acid (PLA): A tissue–engineering study," *J. Biomed. Mat. Res.* 29:1147–1154 (1995).

Chu et al., "Osteochondral repair using perichondrial cells," *Clin. Orthop. Rel. Res.* 340:220–229 (1997).

Ecker and Crooke, "Combinatorial drug discovery: which methods will produce the greatest value?" *Biotechnology* 13:351–360 (1995).

Felgner et al., "Lipofection: A highly efficient, lipid–mediated DNA–transfection procedure," *Proc. Natl. Acad. Sci., USA* 84:7413–7417 (1987).

Gattei et al., "CD30 ligand is frequently expressed in human hematopoietic malignancies of myeloid and lymphoid origin," *Blood* 89(6):2048–2059 (1997).

Jellinek et al., "Potent 2'–amino–2'–deoxyprimidine RNA inhibitors of basic fibroblast growth factor," *Biochem.* 34:11363–11372 (1995).

Lasic, D., "Synthetic lipid microspheres serve as multipurpose vehicles for the delivery of drugs, genetic material and cosmetics," *American Scientist* 80:20–31 (1992).

Lee & Huang, "Folate–targeted, anionic liposome–entrapped polylysine–condensed DNA for tumor cell–specific gene transfer," *J. Biol. Chem.* 271:8481–8487 (1996).

Li and Manolios, "Role of T–cell antigen receptors in rheumatic disease," *Austr. NZ. J. Med.* 23:205–212 (1993).

Lin et al., "Modified RNA sequence pools for in vitro selection," *Nucl. Acids Res.* 22:5229–5234 (1994).

Pagratis et al., "Potent 2'–amino–, and 2'–fluoro–2'–deoxyribonucleotide RNA inhibitors of keratinocyte growth factor," *Nature Biotechnol.* 15:68–73 (1997).

Stribling et al., "Aerosol gene delivery in vivo," *Proc. Natl. Acad. Sci., USA* 89:11277–11281 (1992).

Tam et al., "Biological availability and nuclease resistance extend the in vitro activity of a phosphoraothioate–3'hydroxypropylamine," *Nucl. Acids Res.* 22:977–986 (1994).

Taxman et al., "Receptor–targeted transfection using stable maleimido–transferrin/thio–poly–L–lysine conjugates," *Analyt. Biochem.* 213:97–103 (1993).

Wagner et al., "Transferrin–polycation conjugates as carriers for DNA uptake into cells," *Proc. Natl. Acad. Sci., USA* 87:3410–3414 (1990).

Wagner et al., "Delivery of drugs, proteins and genes into cells using transferrin as a ligand for receptor–mediated endocytosis," *Adv. Drug Deliv. Rev.* 14:113–135 (1994).

Wheeler et al., "A novel cationic lipid greatly enhances plasmid DNA delivery and expression in mouse lung," *Proc. Natl. Acad. Sci., USA* 93:11454–11459 (1996).

* cited by examiner

| TREATMENT | EFFICIENCY (%) |
|---|---|
| DNA+TRANSFERRIN+LIPOSOMES | 25.3+/-4.0 |
| DNA+TRANSFERRIN+POLY-L-LYSINE+LIPOSOMES | 40.8+/-6.7 |
| DNA+COVALENTLY LINKED TRANSFERRIN-POLY-L-LYSINE+LIPOSOMES | 71.1+/-11.6 |

FIG. 5

Mock transfected

Beta-gal transfected

COMPOSITIONS FOR RECEPTOR/ LIPOSOME MEDIATED TRANSFECTION AND METHODS OF USING SAME

This application claims the benefit of U.S. Provisional Application No. 60/074,468, filed Feb. 12, 1998, and is incorporated herein by reference.

This invention was made with government support under grant number AR07484 awarded by the National Institutes of Health. The government has certain rights in the invention.

BACKGROUND OF THE INVENTION

1. Field of the Invention

The present invention relates generally to the delivery of nucleic acid molecules into cells and, more specifically, to compositions and methods for the high efficiency delivery of nucleic acid molecules into cells.

2. Background Information

Methods that allow the introduction and expression of foreign or exogenous nucleic acid molecules into cells in culture are useful for manipulating the function and expression of various genes, as well as for efficiently expressing a desired protein. In addition, the ability to transfer genes to human cells provides the means to treat a wide range of genetic and acquired diseases, including cystic fibrosis, sickle cell anemia, and AIDS. Unfortunately, methods for introducing a gene of interest into a cell have provided relatively low transfection efficiencies or have been successful only in cultured cell lines.

Transfection methods can be used to replace a defective gene or to correct an error in an existing one. Replacement therapy entails inserting a gene into a cell in order to synthesize a gene product that is not being produced or is being synthesized in inadequate amounts. Corrective therapy, on the other hand, attempts to correct an error in a gene by providing conditions for a recombinational event that replaces all or part of the defective gene with the correct DNA sequence.

Various transfection methods have been developed for eukaryotic cells, particularly mammalian cells. Some transfection methods use calcium phosphate or DEAE-dextran as a carrier to promote the uptake of an exogenous nucleic acid molecule. Other methods use "lipofection" techniques, which incorporate the use of synthetic anionic or cationic lipids to effect the transfection. Osmotic shock, treatment of the cells with liposomal inhibitors, and high voltage electric pulses, which create pores in cell membranes, also have been used in attempts to enhance transfection efficiencies. However, the efficiencies obtained by these methods are relatively low, ranging from 0.001% to 1%, depending on the recipient cell line.

In further efforts to increase the efficiency of introducing nucleic acid molecules into cells, viral vectors have been used. For example, when retroviral vectors are used, the introduced DNA replaces some of the retroviral genes required for the production of viral structural proteins while the viral sequences directing integration into the cellular DNA remain intact. However, the use of retroviral vectors is limited to dividing cells. Adenovirus vectors also have been used with fairly high efficiency, but they only infect specific cell types. In addition, the use of viral vectors is limited by the induction of an immune response against the viral components of the vectors.

Other methods of introducing a nucleic acid molecule into a cell include complexing the nucleic acid molecule with proteins that bind to specific receptors expressed by the target cells, or by incorporating the nucleic acid molecule into liposomes, which fuse with the target cell membrane. Gene transfection of mammalian cells using cationic liposomes, for example, has achieved an efficiency of up to 15% and transferrin-poly-L-lysine mediated transfection has yielded 7% to 8% transfection efficiency. A transfection efficiency of about 90% has been achieved in a cultured cell line using a combination of transferrin and cationic liposomes.

While these approaches represent an improvement over prior techniques, a need exists for compositions and methods for introducing a nucleic acid molecule into any target cell, particularly primary mammalian cells, with efficiencies of about 50% or greater. The present invention satisfies this need and provides related advantages as well.

SUMMARY OF THE INVENTION

The present invention provides a composition for introducing a nucleic acid molecule into a target cell, comprising a liposome, ligand and polymeric scaffold, wherein the ligand can bind to a receptor on the target cell. The liposome can be cationic. The ligand can be attached to the polymeric scaffold. The polymeric scaffold can be positively charged. Thus, for example, the invention provides a composition comprising a cationic liposome, and transferrin, wherein the transferrin is attached to poly-L-lysine.

The invention also provides a method for introducing a nucleic acid molecule into a target cell by contacting the target cell with the nucleic acid molecule, a liposome, a ligand and a polymeric scaffold, wherein the ligand binds to a cell surface receptor on the target cell. The ligand can be attached to the polymeric scaffold. The polymeric scaffold can be positively charged. Thus, for example, the invention provides a method for introducing a nucleic acid molecule into primary mammalian cells, wherein at least about 50% of the transfected cells contain the introduced nucleic acid molecule. A method of the invention further comprises permeabilizing the target cells to facilitate uptake of the nucleic acid molecule.

BRIEF DESCRIPTION OF THE DRAWINGS

The file of this patent contains atleast one drawing executed in color. Copies of this patent with color drawings will be provided by the Patent and Trademark Office upon request and payment of the necessary fee.

FIG. 1A provides a schematic representation for extracting primary perichondrial cells yielding 1 million cells/100 mg wet weight tissue in less than 48 hours. FIG. 1B provides a schematic representation of the transfection method of the present invention. Specifically, FIG. 1B presents a schematic of a three step ex-vivo gene therapy protocol used to achieve very high efficiency of gene transfection into primary perichondrium derived cells. Components of the method are indicated.

FIG. 2 shows transfection of primary perichondrium cells in monolayer by method illustrated in FIG. 1. β-galactosidase activity was monitored by in situ X-gal staining (blue cells).

FIG. 3 is a graphical representation of relative levels of β-gal activity, assessed using the o-nitrophenyl-D- galactopyranoside (ONPG) reaction measured as optical density at 420 nm. The left bar represents β-gal activity resulting from transfection using liposomes and a nucleic acid molecule encoding β-gal. The right bar represents β-gal activity when a ligand (transferrin) and positively charged polymeric scaffold (poly-L-lysine) complex (TPL) is included with the liposome and nucleic acid molecule encoding β-gal. A significant increase in β-gal activity and, therefore, transfection efficiency, is observed when the β-gal nucleic acid molecule is transfected using the complex of the invention.

Figure 4A:
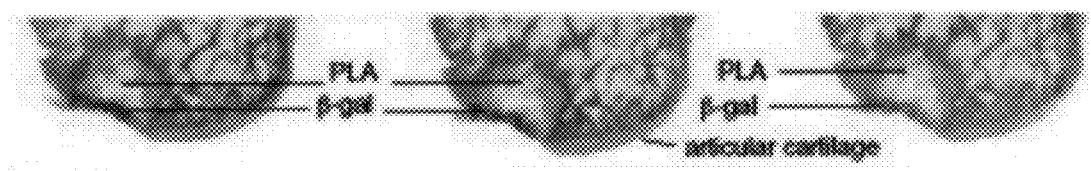
Figure 4B:
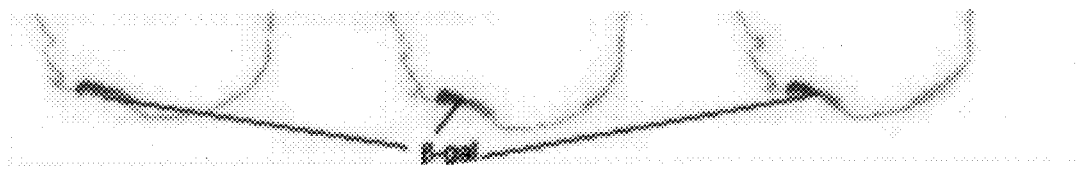
Figure 4C:
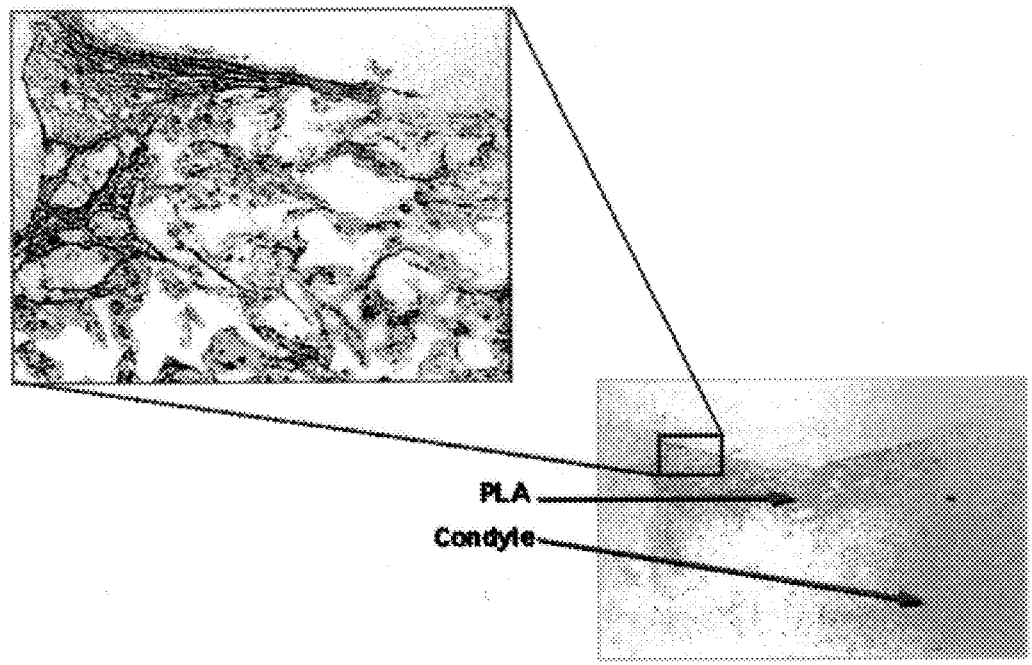

FIGS. 4A to 4C provide an in vivo assessment of transfected primary perichondrial cells seven days post-implantation.

FIG. 4A demonstrates an in vivo assessment of transfected primary perichondrial cells that were implanted into osteochondral defects in femoral condyles of mature rabbits. β-gal activity was assessed, 7 days post implantation, by X-gal activity (blue). Cells were also stained with eosin (red). "PLA" indicates polylactic acid. The cells are shown at a 2.5×magnification.

FIG. 4B shows β-gal activity by X-gal staining alone (no eosin). The cells are shown as a 2.5×magnification.

FIG. 4C shows an X-gal stained section of the cells at higher magnification (200×).

FIG. 5 shows efficiency of gene transfection into permebilized primary perichondrial cells. More specifically, FIG. 5 recites the tranfection efficiencies resulting from transfection of permeabilized primary cells using (1) liposomes, a ligand (transferrin) and a nucleic acid molecule encoding β-gal; (2) a ligand (transferrin) and positively charged polymeric scaffold (poly-L-lysine) included with the liposome and nucleic acid molecule encoding β-gal; and (3) a ligand (transferrin) covalently linked to a positively charged polymeric scaffold (poly-L-lysine) included with the liposome and nucleic acid molecule encoding β-gal (the DPTLL complex). A significant increase in transfection efficiency is observed when the β-gal nucleic acid molecule is transfected using the complex of the invention.

Figure 6A:
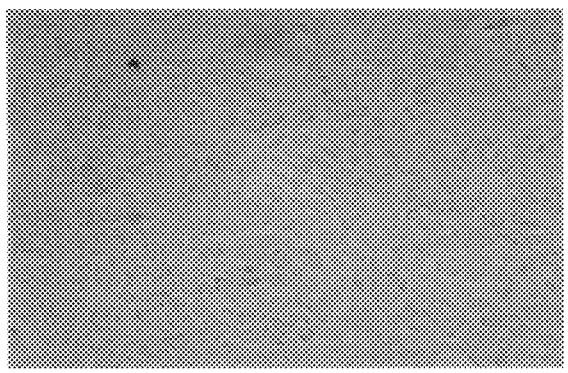

FIG. 6A shows primary rabbit chondrocytes mock transfected with a plasmid DNA.

Figure 6B:
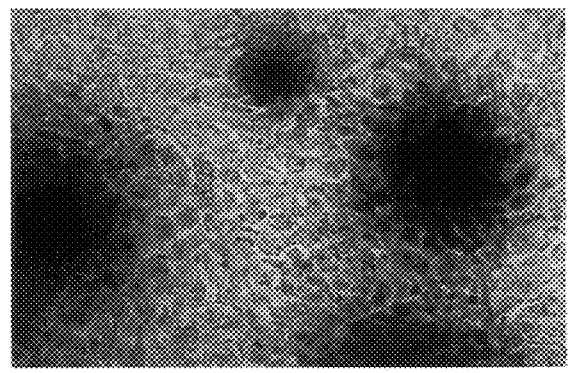

FIG. 6B shows primary rabbit chondrocytes transfected with β-gal expression vector using a method of the invention—i.e., ligand (transferrin) and positively charged polymeric scaffold (poly-L-lysine) complex (TPL) included with liposome. This transfection of previously permeabilized chondrocytes was more than 70% efficient. β-gal activity of transfected cells was identified by blue staining in the presence of X-gal.

Figure 7:
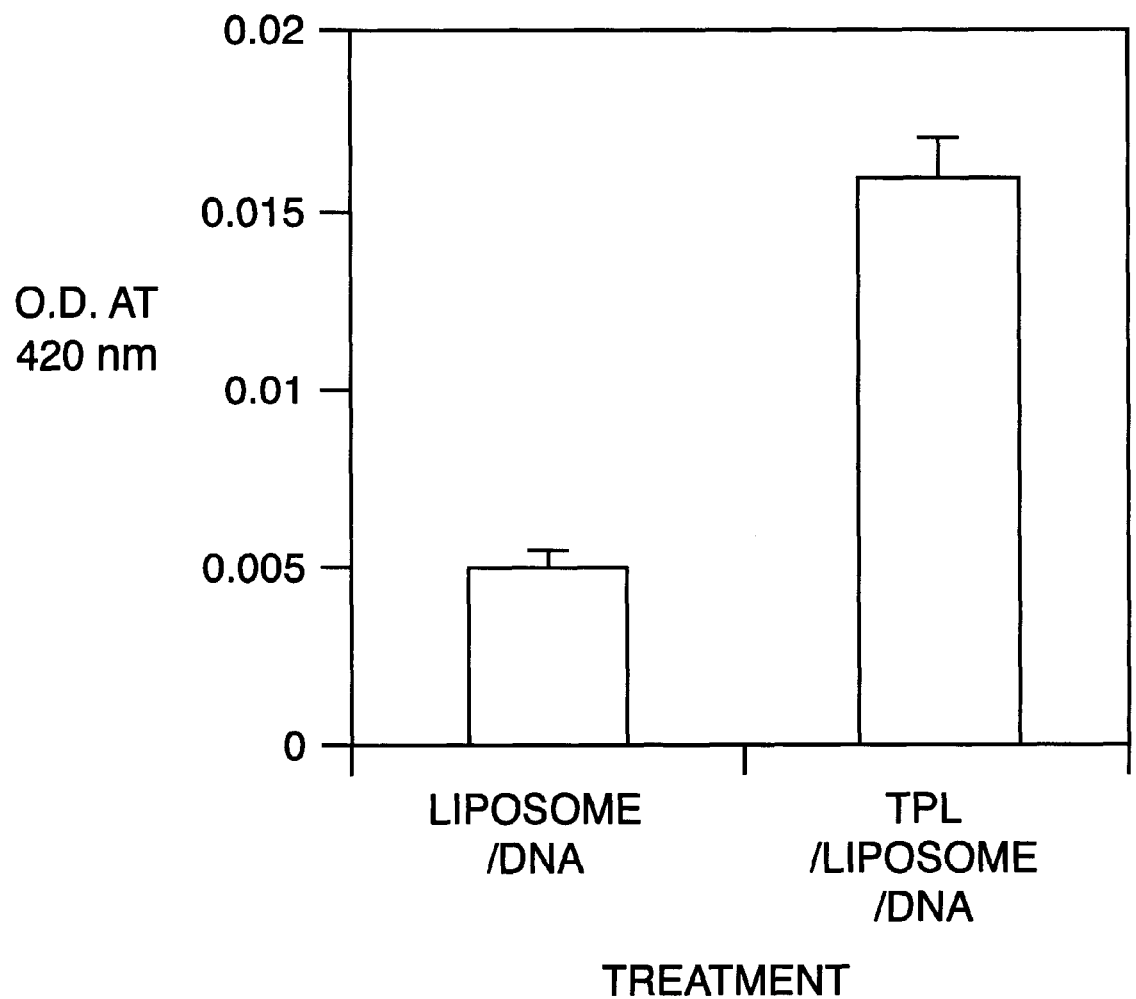

FIG. 7 shows the relative levels of ONPG reaction (O.D. at 420 nm) of mock transfected and β-gal transfected primary chondrocytes.

DETAILED DESCRIPTION OF THE INVENTION

The present invention provides a composition for high efficiency receptor/liposome mediated delivery of nucleic acid molecules into cells. As disclosed herein, a composition of the invention is useful for introducing a nucleic acid molecule into a cell, ex vivo or in vivo, with transfection efficiencies of about 50% or greater. In particular, a composition of the invention is useful for introducing a nucleic acid molecule into a primary cell, for example, primary mammalian cells such as human cells.

As used herein the term "transfection efficiency" refers to the percentage of target cells, within a population of target cells, that contain an introduced exogenous nucleic acid molecule. Transfection efficiency can be determined by transfecting a nucleic acid molecule encoding a reporter gene, for example, β-gal, into a population of target cells and determining the percentage of cells having β-gal activity (see Example I). Thus, transfection efficiency can be determined by assaying for the gene product encoded by the introduced nucleic acid molecule. Reference herein to "high transfection efficiency" or the like refers to a transfection efficiency of at least about 50%.

Various compositions and methods to deliver nucleic acid molecules into cells have been used. For example, gene transfection of mammalian cells has been performed using molecular conjugates, which can be prepared by chemically linking receptor ligands with polycations (Wagner et al., Adv. Drug Deliv. Rev. 14:113–135 (1994), which is incorporated herein by reference). The polycation component of the conjugate carries the DNA, while the ligand targets cell surface receptors. Such conjugates including the linked DNA, are then internalized into the target cells. Transferrin and poly-L-lysine mediated transfection, for example, has yielded a 7% to 8% transfection efficiency (Wagner et al., Proc. Natl. Acad. Sci., USA 87:3410–3414 (1990) and Taxman et al., Analyt. Biochem. 213:97–103 (1993), each of which is incorporated herein by reference). However, these methods result, at best, in about 15% of the target cell population expressing the gene of interest.

Other methods of transfection employ cationic liposomes, where the liposomes encapsulate the DNA, thereby facilitating the introduction of the encapsulated DNA into the cells by fusion with the plasma membrane or by endocytosis. Transfection efficiencies ranging from about 1% to 15% have been achieved by using cationic liposomes (Felgner et al., Proc. Natl. Acad. Sci., USA 84:7413–7417 (1987); Wheeler et al., Proc. Natl. Acad. Sci., USA 93:11454–11459 (1996), each of which is incorporated herein by reference).

Combinations of transfection methods also have been used in an attempt to improve transfection efficiency. A transfection efficiency of up to 100% in HeLa cells has been reported using a combination of transferrin and cationic liposomes (Cheng, Human Gene Ther. 7:275–282 (1996), which is incorporated herein by reference).

However, the method of Cheng was performed without using a polymeric scaffold such as poly-L-lysine, much less attaching the ligand, transferrin, to a polymeric scaffold. Moreover, the method of Cheng was performed using HeLa cells, which are a well established cell line, and such high transfection efficiencies have not yet been reported for primary mammalian cells. Cheng also did not permeabilize the cells prior to performing the transfection.

The method of Cheng, supra, (1996) was examined in parallel with a method of the invention to compare transfection efficiencies for primary mammalian cells. In particular, primary perichondrial cells were transfected with DNA, cationic liposomes and transferrin, as described by Cheng, and a transfection efficiency of about 25% was obtained. In comparison, transfection of using DNA, transferrin, poly-L-lysine and cationic liposomes, wherein the transferrin was covalently linked to the poly-L-lysine, according to a method of the invention resulted in greater than 70% transfection efficiency. In a control experiment, DNA, transferrin, poly-L-lysine and cationic liposomes, wherein the transferrin and poly-L-lysine were not linked, were used for transfection and a transfection efficiency of about 40% was obtained. These results indicate that a method of the invention provides high transfection efficiency, whereas the method of Cheng does not produce high transfection efficiency as defined herein.

The present invention provides a composition of matter useful for introducing exogenous nucleic acid molecules into target cells with high efficiency. A composition of the invention comprises a nucleic acid molecule, a cationic liposome, and a ligand that can bind to a cell surface receptor expressed by the target cells, wherein the ligand is attached to a positively charged polymeric scaffold (see FIG. 1B). A composition of the invention is distinguishable, for example, from the composition used by Cheng, supra, (1996), in that a composition of the invention comprises a polymeric scaffold.

As used herein, the term "introducing" when used in reference to an exogenous nucleic acid molecule, means that the nucleic acid molecule is delivered into a target cell; i.e., the nucleic acid molecule is transfected into the target cell. The term "target cell" is used herein to mean any cell into which an exogenous nucleic acid molecule is to be introduced. In particular, however, a target cell is characterized in that it expresses a particular cell surface receptor, which can bind the ligand component of a composition of the invention.

If desired, a nucleic acid molecule to be introduced into a target cell can be contained in a vector, which can be derived, for example, from a plasmid, bacteriophage or plant or animal virus. Such vectors can contain an origin of replication recognized by an appropriate host cell and, in the case of expression vectors, can contain a promoter or other regulatory region useful in a particular host cell or target cell. For example, a vector comprising the open reading frame of the active form of the β-gal gene ligated downstream of a human cytomegalovirus (CMV) promoter/enhancer sequence in a plasmid carrying the expression cassette for a gene for ampicillin resistance was used to determine the transfection efficiency obtained using a composition and a method of the invention (Example I). One skilled in the art would know how to make and use or otherwise obtain other vectors (see, for example, Sambrook et al., *Molecular Cloning: A Laboratory Manual* (Cold Spring Harbor Press; Cold Spring Harbor, N.Y.; 1989), which is incorporated herein by reference).

A composition of the invention also comprises a liposome, including a cationic liposome. As used herein, the term "liposome" refers to a vesicle bounded by a lipid bilayer. A "cationic liposome" has a net positive charge. Liposomes, including cationic liposomes, are well known in the art and can be prepared using routine methods (see, for example, Brant et al., *Am. Fed. Med. Res.* 45 (1):159A (1997), which is incorporated herein by reference; Feigner et al., supra (1987); and Wheeler et al., supra (1996)) or using commercially available kits such as DOTAP (Avanti Polar Lipids, Alabaster, Ala.); DOSPA (Life Technologies, Inc., Gaithersburg, Md.); and DDAB (Kodak, Rochester, N.Y.). Anionic liposomes and synthetic lipid microspheres can also be used in the present invention (see, for example, Lasic, *American Scientist* 80:20–31 (1992), which is incorporated herein by reference).

As used herein, the term "ligand" is used broadly herein to refer to a molecule that can bind to a receptor expressed on the surface of a target cell or, conversely, to a receptor that can bind a molecule expressed on the surface of a target cell. For example, the "ligand" can be transferrin, which can bind to a transferrin receptor expressed on the surface of a target cell such as a perichondrial cell (see Examples I and II). In addition, the "ligand" can be, for example, an anti-CD4 antibody, which binds to CD4 expressed on a target cell such as a T cell.

In a composition of the invention, the ligand is attached to a positively charged polymeric scaffold by a covalent bond or other bond that is relatively stable under physiological conditions, including in vivo or in tissue culture. Thus, the ligand can be attached by noncovalent or ionic interaction between the positively charged polymeric scaffold and the ligand, provided the ligand is sufficiently anionic such that the interaction is maintained under physiological conditions. The use of a tether can facilitate binding and optimize the ratio of the scaffold to the ligand. A tether can be, for example, biotin, which is attached to the scaffold and binds avidin, which can be attached to the ligand.

A ligand useful in the invention can be any ligand that can bind to a receptor expressed on the surface of the target cell; or any receptor or other binding molecule that can bind to a molecule expressed on the surface of the target cell. For example, the ligand can be transferrin, which is covalently bound to poly-L-lysine (see Examples I and II). Other ligands useful in a composition of the invention include, for example, insulin, folate or cholera toxin (Cheng, supra, (1996); Lee and Huang, *J. Biol. Chem.* 271 (14):8481–8487 (1996), which is incorporated herein by reference). In addition, other ligands that can be internalized upon binding to their receptors would be known to one in the art and would depend, for example, on the particular target cell to be transfected. Thus, the selection of the ligand will be based on the desired target cell. Other ligands and receptors include, for example: T cell receptor and T cell antigen pairs (Lee et al., *Austr. New Zeal. J. Med.* 23:205–212 (1993)); anti-idiopathic antibodies for human non-Hodgkin's lymphoma; CD30 receptor and ligand pair for acute myeloid leukemias, B cell lineage acute lymphoblastic leukemias, Hairy cell leukemia, and B cell non-Hodgkin's lymphoma (Gattei et al., *Blood* 89:2048–2059 (1997), which is incorporated herein by reference); somatostatin receptors and ligand pairs for tumors and cancers to block the hypersecretion of growth hormones in acromegaly; selectins, for example, P-selectin and P-selectin specific ligands; cadherins, for example, cadherin-11; or c-kit receptor and its ligand, stem cell factor.

An advantage of the present invention is the ease of preparation of the composition, since all of the components are commercially available. Reagents such as transferrin and poly-L-lysine, for example, can be purchased from Sigma Chemical Co. (St. Louis, Mo.). In addition, a composition of the invention poses only a low risk of generating a host immune response. For example, a ligand prepared from a particular animal source can be used for transfecting cells of that same animal species without concern of generating a host immune response against the ligand. There is also a minimal risk of immune response to the liposomes, as liposome toxicity studies have shown that they cause little or no host inflammatory or immune response (Stribling et al., *Proc. Natl. Acad. Sci., USA* 89:11277–11281 (1992); Alton et al., *Nature Genet.* 5:135–142 (1993)). Thus, a composition of the invention provides an advantage over the use of viral vectors, for example, in that the likelihood of an adverse immune response is minimized.

A composition of the invention contains a positively charged polymeric scaffold. As used herein, the term "polymeric scaffold" means a polymer having a net positive or neutral charge such that it can interact and form a complex with a negatively charged nucleic acid molecule. It should be understood that a polymeric scaffold can contain one or more units that have a negative charge, provided the the polymer has a net positive or neutral charge.

A positively charged polymeric scaffold is exemplified herein by poly-L-lysine. Other scaffolds of the invention can be homo-polymeric amino acids, hetero-polymeric amino acids, amino acids not covalently bonded to each other, polymers containing positively charged moieties such as amine groups, poly-spermine or poly-spermidines. The term "homo-polymeric amino acids" means a covalently bonded polymer of the same amino acids either charged or uncharged and, which may interact with the nucleic acid molecule specifically or non-specifically. Conversely, the term "hetero-polymeric amino acids" means a covalently bonded polymer of different amino acids either charged or uncharged and, which may interact with the nucleic acid molecule specifically or non-specifically. Positively charged polymeric scaffolds with modifications or variations to their lengths are contemplated within the present invention, provided they allow high transfection efficiency as defined herein. For example, the molecular weight of poly-L-lysine can be from 15 kDa to 150 kDa. Modifications and or variations in the length of the positively charged polymeric scaffold can be made and the effect they have on transfection efficiency can be determined using methods as disclosed herein or methods otherwise known in the art.

As used herein, the term "nucleic acid molecule" is used in its broadest sense to mean two or more nucleotides or nucleotide analogs linked by a covalent bond. Thus, the term "nucleic acid molecule" encompasses oligonucleotides, which generally are less than about fifty nucleotides in length, and polynucleotides, which can be essentially any length, and can comprise DNA such as a cDNA or a gene, or RNA. The term "exogenous," when used in reference to a nucleic acid molecule, means that the nucleic acid molecule is from a source other than the target cell, into which the nucleic acid molecule is to be introduced. It should be recognized, however, that the exogenous nucleic acid molecule also can be from other cells of the same type as the target cells.

In general, the nucleotides comprising a nucleic acid molecule are naturally occurring deoxyribonucleotides such as adenine, cytosine, guanine or thymine linked to a 2'-deoxyribose, or ribonucleotides such as adenine, cytosine, guanine or uracil linked to ribose. However, a nucleic acid molecule also can comprise nucleotide analogs, including non-naturally occurring synthetic nucleotides or modified naturally occurring nucleotides. Such nucleotide analogs are well known in the art and commercially available, as are nucleic acid molecules containing such nucleotide analogs (Lin et al., *Nucl. Acids Res.* 22:5220–5234 (1994); Jellinek et al., *Biochem.* 34:11363–11372 (1995); Pagratis et al., *Nature Biotechnol.* 15:68–73 (1997)). The covalent bond linking the nucleotides of a nucleic acid molecule generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic nucleic acid molecules (see, for example, Tam et al., *Nucl. Acids Res.* 22:977–986 (1994); Ecker and Crooke, *BioTechnology* 13:351360 (1995)). Where it is desired to synthesize a nucleic acid molecule to be introduced into a target cell, the artisan will know that the selection of particular nucleotides or nucleotide analogs and the covalent bond used to link the nucleotides will depend, in part, on the purpose for which the nucleic acid molecule is prepared.

A nucleic acid molecule comprising naturally occurring nucleotides and phosphodiester bonds can be chemically synthesized or can be produced using recombinant DNA methods, using an appropriate nucleic acid molecule as a template. In comparison, a nucleic acid molecule comprising nucleotide analogs or covalent bonds other than phosphodiester bonds generally will be chemically synthesized, although an enzyme such as T7 polymerase can incorporate certain types of nucleotide analogs and, therefore, can be used to provide such a nucleic acid molecule recombinantly from an appropriate template (Jellinek et al., supra, (1995)).

Compositions of the invention provide a means for high efficiency transfection of target cells. As such, the invention provides methods of transfecting target cells with high efficiency. In one embodiment, a method of the invention is performed by permeabilizing the target cells and contacting the cells with a composition comprising an exogenous nucleic acid molecule, a cationic liposome and a ligand that binds to a receptor expressed on the surface of the target cells, wherein the ligand is bound to a positively charged polymeric scaffold. The target cells can be permeabilized using, for example, lysolecithin, TWEEN-20, NP-40, TRITON X-100, phosphatidylcholine or phospholipases. Target cells also can be permeabilized by osmotic shock or high-voltage electric pulses.

Methods of the invention can be performed in vivo or ex vivo. For ex vivo transfection, the target cells are removed from a subject, for example, by a biopsy procedure. An appropriate ligand is selected based on knowledge of a cell surface receptor, for example, expressed by the target cell. The target cells can be permeabilized, if desired, and contacted with a composition comprising an exogenous nucleic acid molecule, a liposome, a ligand and a polymeric scaffold, wherein the ligand can bind to a cell surface receptor. The transfected cells can then be implanted into a subject, generally the subject from which the cells originally were obtained. Thus, the invention provides a means of performing ex vivo gene therapy.

Figure 2:
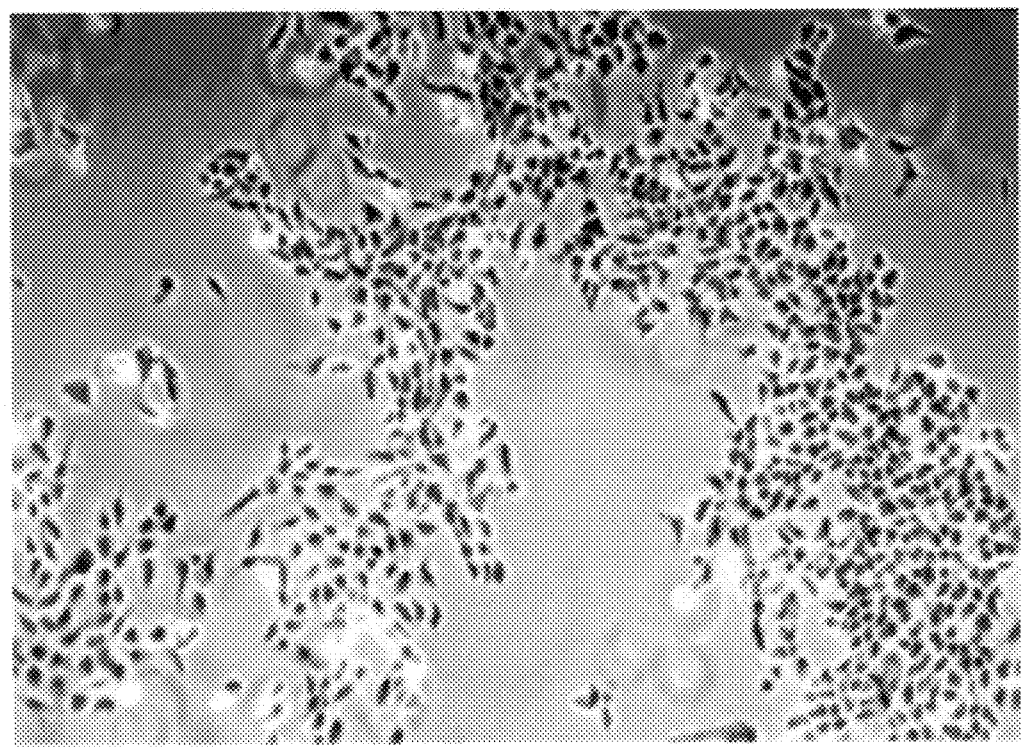
FIG. 2 demonstrates β-galactosidase (β-gal) activity in primary perichondrial cells transfected with a β-gal reporter gene using a method of the invention. Specifically.

A method of the invention is exemplified by the introduction of an exogenous nucleic acid molecule encoding β-gal into primary perichondrial cells. As evidenced by identifying β-gal activity, high transfection efficiency of about 70% or greater was obtained (see FIGS. 2, 5 and 6). Furthermore, the transfected perichondrial cells were seeded into polylactic acid cores and implanted into artificially created osteochondral defects in the femoral condyles of mature rabbits (see Example I and FIG. 4). As disclosed herein, expression of the introduced nucleic acid molecule was observed 7 days post-implantation (see FIG. 4). Thus, the compositions and methods of the invention provide a means for high transfection efficiency of an exogenous nucleic acid molecule into primary cells and expression of a gene product encoded by the introduced nucleic acid molecule occurs when the cells are transplanted into a subject, demonstrating that the invention is useful for ex vivo gene therapy.

The invention also provides methods of introducing an exogenous nucleic acid molecule into a target cell in vivo by directly injecting a composition of the invention, containing the exogenous nucleic acid molecule, into the desired site in a subject. For example, a composition of the invention can be administered directly into the articular region of a knee joint having an osteochondral defect and, if desired, a cell permeabilizing agent also can be administered. Cells can be permeabilized in vivo by using detergents that are tethered to a ligand-positively charged polymeric scaffold complex. Specific enzymes that result in permeabilizing the cell, such as phospholipases can also be used. Toxins that disrupt the membrane can also be used to selectively create pores in the cell membrane. The in vivo methods can be useful for effecting high transfection efficiency of an exogenous nucleic acid molecule into particular cells in a subject. In particular, where the selected target cell expresses a unique cell surface receptor, the ligand can be selected such that only the desired target cells are transfected.

The present invention also provides a kit, comprising a liposome, a ligand and a polymeric scaffold. A kit of the invention also can contain a cell permeabilizing agent and, if desired, a control exogenous nucleic acid molecule, which can provide a means to confirm high transfection efficiency.

A kit of the invention can be particularly useful if it contains a panel of ligand/scaffold combinations. For example, a kit of the invention can contain various different ligands such as insulin, folate, cholera toxin and epidermal growth factor, each covalently linked to a positively charged polymeric scaffold or to various positively charged polymeric scaffolds such as poly-L-lysine of varying molecular weights. Thus, the skilled artisan, having selected a particular target cell to transfect, need only obtain from the kit the appropriate ligand/scaffold complex depending the cell surface receptor expressed by the target cells. A kit can further comprise, for example, cationic liposomes and, if desired, reagents such as buffers and the like for performing the transfection.

The following examples are intended to illustrate but not limit the invention.

EXAMPLE I

High Efficiency Transfection of Primary Mammalian Cells

This example describes the preparation and high efficiency transfection of primary mammalian perichondrial cells.

A. Cell Preparation

New Zealand white rabbits were sacrificed according to approved protocols. The costal ribs were removed using sterile procedures and the ribs cleaned away from adhering tissues by the use of sterile surgical instruments. The rib perichondrium was isolated by breaking the ribs and peeling off the perichondrium tissue. The isolated perichondrium was washed three times in penicillin and streptomycin containing buffered salt solution.

Figure 1A:
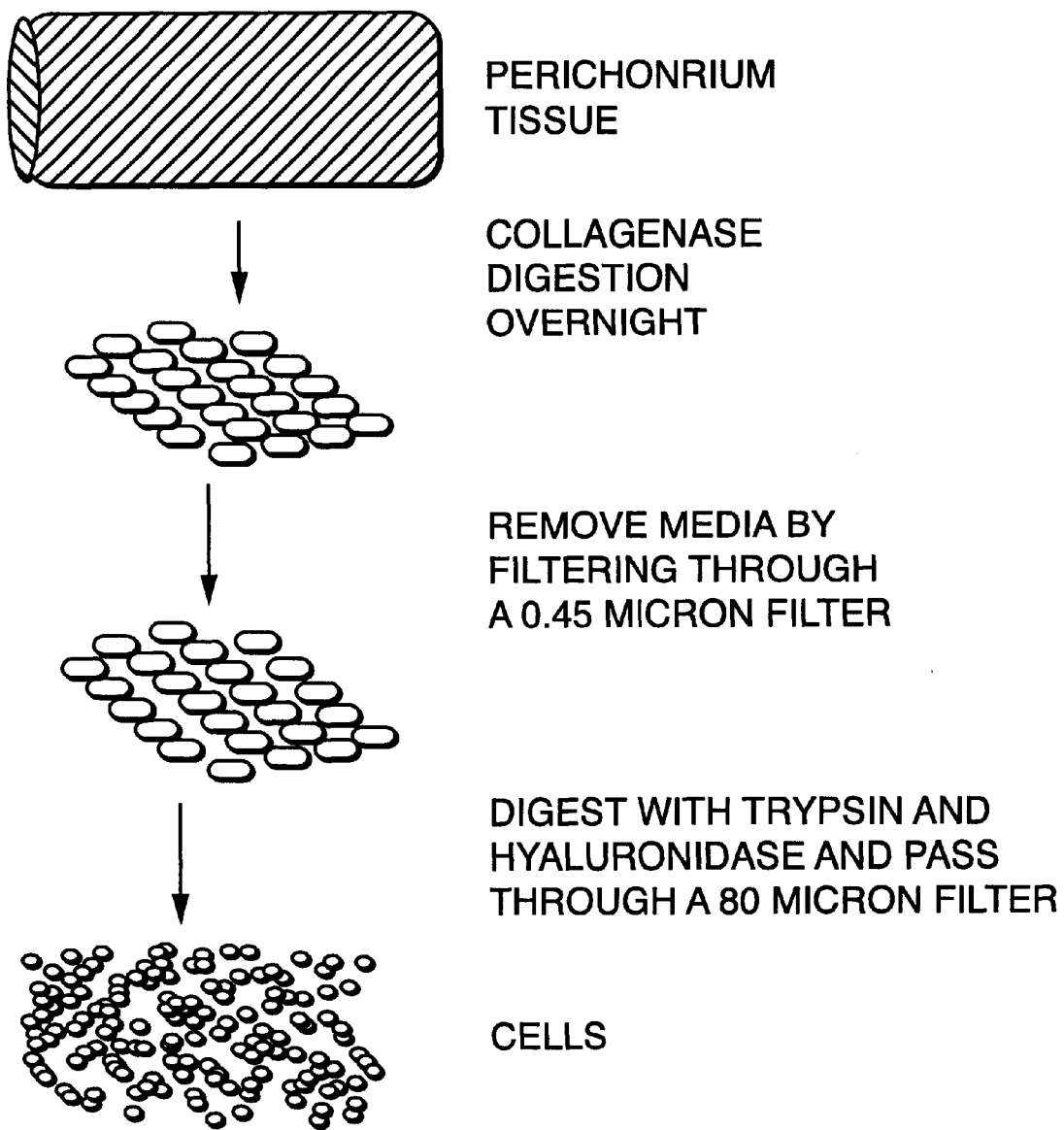
FIGS. 1A and 1B show methods for isolating and transfecting perichondrial cells using a method of the invention.

Perichondrium cells were isolated by incubating the perichondrium tissue overnight at 37° C. under sterile conditions in a 0.1% collagenase Dulbecco's modified Eagle's medium (DMEM) with 10% fetal bovine serum (FBS) containing 1% penicillin and streptomycin. Cells and tissue debris were isolated away from the medium by passage through a 0.45 micron sterile filer, then were enzymatically digested for 30 min to 5 hr with 0.1% hyaluronidase and trypsin. Purification of the cells was accomplished by passage through a 80 micron filter under sterile conditions (see FIG. 1A).

The primary perichondrial cells were deposited on tissue culture plates in DMEM and 10% FBS under sterile conditions at 37° C. The cells were allowed to proliferate and to achieve about 70% to 80% confluence. The cells were permeabilized by incubation with lysolecithin at 0.0035% w/v for 2 min, then washed with serum free medium.

B. Transfection of Primary Perichondrial Cells

The open reading frame of the active form of the β-gal gene downstream of a human CMV promoter/enhancer sequence in a plasmid carrying the expression cassette for a gene for ampicillin resistance was purchased from Promega Inc. (Madison, Wis.). The plasmid was purified by double CsCl equilibrium density centrifugation. Transferrin and poly-L-lysine (70 KDa) were purchased from Sigma Chemical Co. (St. Louis, Mo.). Transferrin was covalently linked to poly-L-lysine using a cross-linking procedure described in Taxman et al., supra, (1993). Cationic liposomes were prepared by mixing L-α-phospatidyl-ethanolamine, dioleoyl with an equal volume of dimethyldioctadecyl-ammonium bromide in chloroform. The mixture was heated to 37° C. using a rotovap evaporator. The mixture was resuspended in sterile filtered water, sonicated and analyzed under a microscope to achieve optimal dispersion of liposomal particles.

Figure 1B:
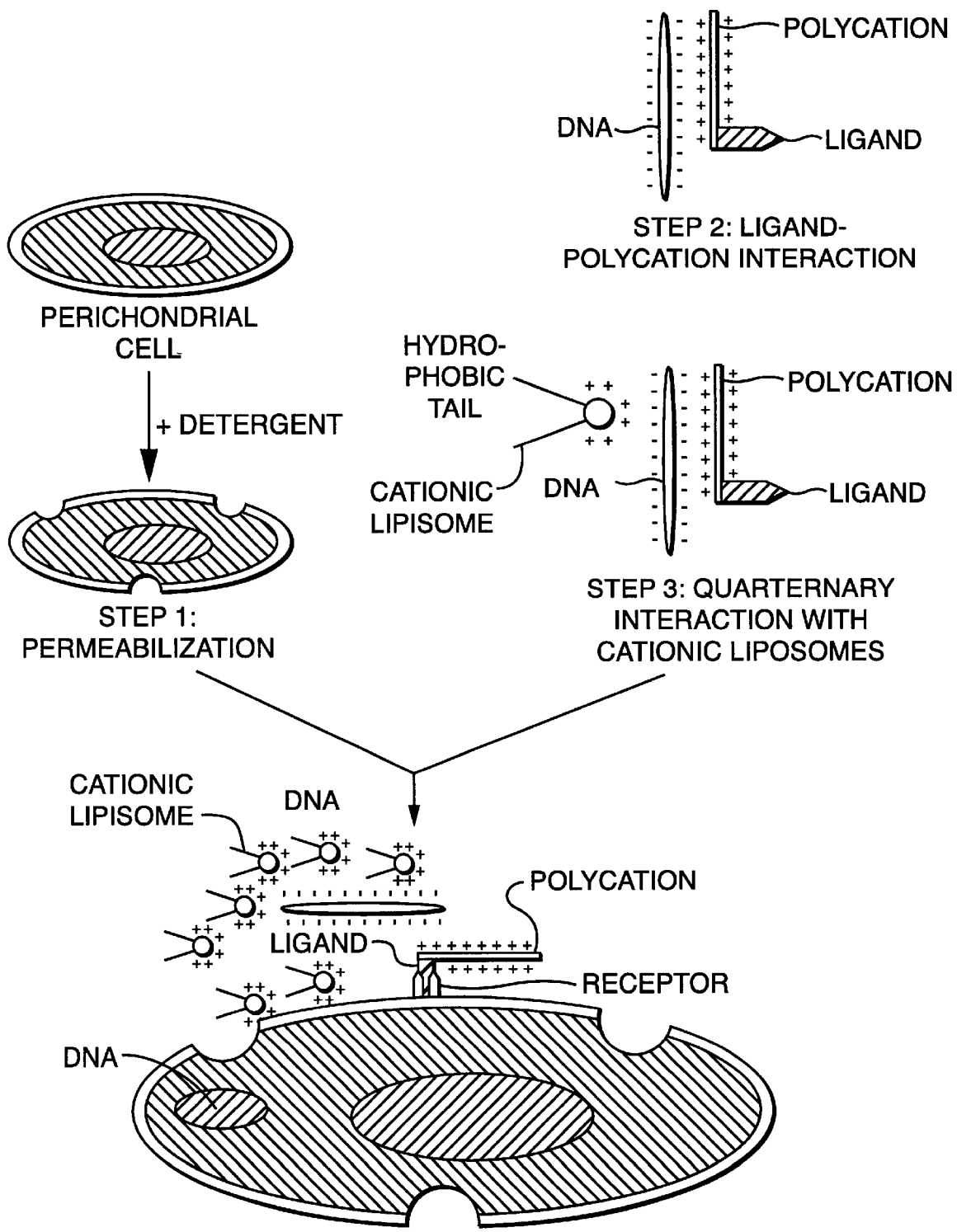

The purified plasmid was incubated in the presence of the transferrin/poly-L-lysine to form a DNA/transferrin/poly-L-lysine complex (see FIG. 1B). The complexes were added to the liposomes in DMEM and allowed to form complexes for 15 to 20 min. The DNA/transferrin/poly-L-lysine/liposome complexes then were incubated in serum free DMEM with the permeabilized perichondrial cells and incubated at 37° C. for 5 hr. The medium was refreshed with DMEM containing 10% FBS and incubation was continued for 48 hr. For comparison of transfection efficiencies, a separate incubation was performed using only DNA and liposomes. Control experiments utilized permeabilized cells incubated with medium lacking DNA or liposomes.

Forty-eight to sixty hours after transfection, the cells either were resuspended in 0.25 M Tris pH 8 and lysed by repeated freeze thaw cycles or the cells were fixed with glutaraldehyde for an in-plate β-gal assay. The cells were fixed in 0.25% v/v glutaraldehyde in 1×phosphate buffered saline (PBS). The fixed cells were then stained with X-gal solution at 37° C. for up to eight hours. The amount of β-gal activity in lysed cells was determined by the ONPG reaction and the absorbance determined at 420 nm. The number of β-gal positive cells was determined by counting under a microscope. A transfection efficiency greater than 70% was obtained in cells transfected with the DNA/transferrin/poly-L-lysine/liposome complex. In comparison, in cells transfected with the DNA and liposomes, alone, the transfection efficiency was about 15% (see FIG. 3).

C. In vivo Implantation of Transfected Cells

β-gal gene expression was allowed to proceed for 12 hr, then the cells were seeded into a polylactic acid (PLA) scaffold (Chu et al., J. Biomed. Mat. Res. 29:1147–1154 (1995) and Chu et al., Clin. Orthop. Rel. Res. 340:220–229 (1997), each of which is incorporated by reference herein). Standard surgical and animal care procedures were used to create a 3 mm×3.7 mm full thickness articular cartilage defect in the rabbit femoral condyle (Chu et al., supra, (1995) and Chu et al., supra, (1997)). The defect was plugged with the transfected cell/PLA scaffold, the knee was sutured and the rabbits were cared for under standard conditions.

Figure 3:
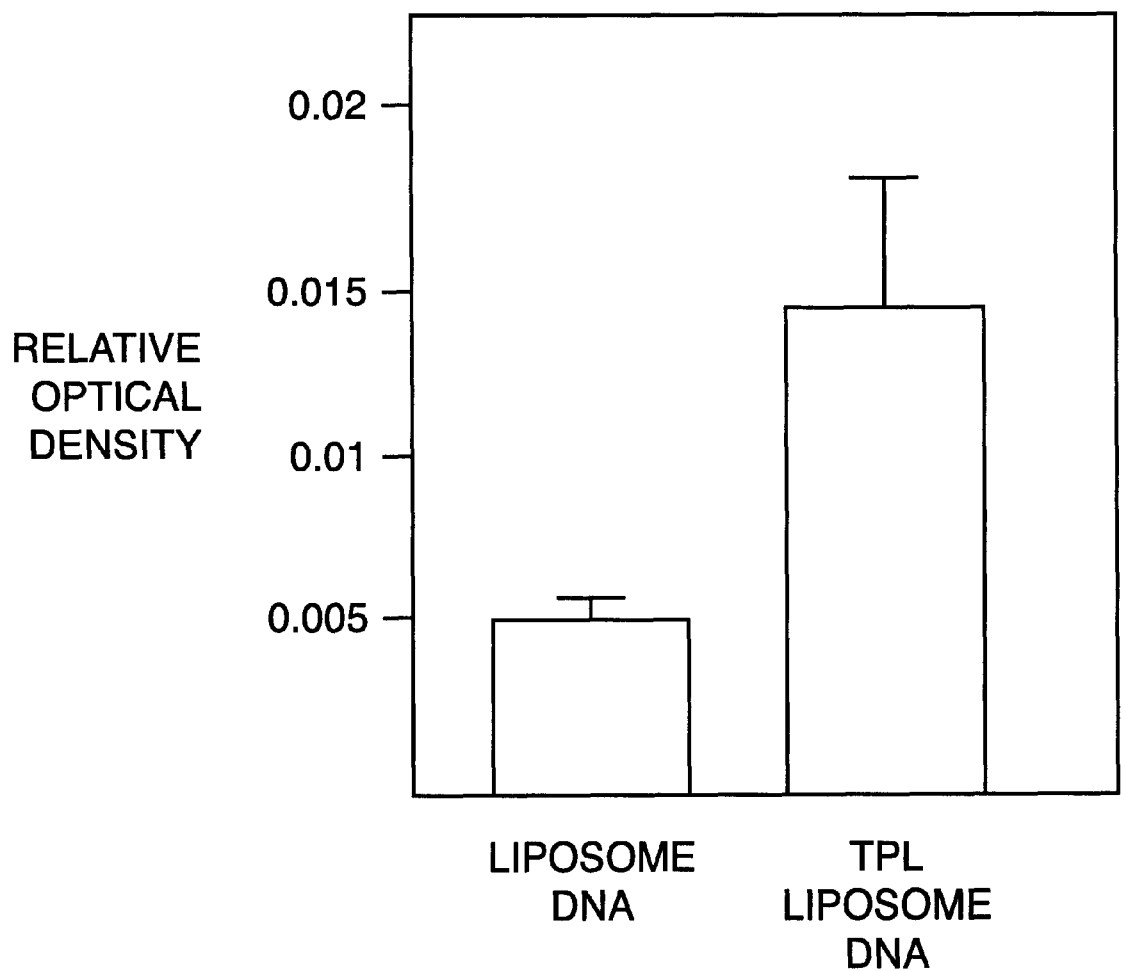

The femoral condyles were harvested after one week and β-gal activity was examined as discussed above (FIG. 4). The ONPG reaction indicated that the inclusion of transferrin/poly-L-lysine enhanced the transfection efficiency significantly as measured by optical density at 420 nm (FIG. 3). The results also demonstrated that the product encoded by the transfected nucleic acid molecule was still expressed one week after transfection (FIG. 4).

These results demonstrate that high transfection efficiency of primary cells can be obtained using the compositions and methods of the invention and that expression of the exogenous nucleic acid molecule introduced into the transfected cells continues in vivo.

EXAMPLE II

High Efficiency Transfection of Primary Mammalian Cells

This example describes the preparation and high efficiency transfection of primary mammalian perichondrial cells.

A. Cell Preparation

New Zealand white rabbits were sacrificed according to approved protocols. The articular cartilage from femoral condyles and tibial plateau was isolated. The chondrocytes were isolated by enzymatic extraction. The cells were allowed to attach and achieve 70% confluence in culture medium (MEM+10% FBS) within 48 hours and were washed in serum free medium. These cells were permeabilized with lysolecithin.

B. Transfection of Primary Perichondrial Cells

The DNA (β-galactosidase gene driven by CMV-promoter/enhancer) construct was purified by double CsCI equilibrium density centrifugation. Permeabilized cells incubated with media lacking DNA or liposomes were used as controls. The previously permeabilized cells were transfected with Transferrinpoly-L-lysine (TPL)/liposome/DNA mixture.

Forty-eight to 60 hours post-transfection, the cells were lysed or the plates were fixed in glutyraldehyde for in-plate β-galactosidase assay. The amount of β-gal activity in lysed cells was assessed for ONPG reaction by determining absorbance at 420 nm and the number of β-gal positive cells stained blue with X-gal was carefully counted under the microscope.

The efficiency of transfection was determined to be consistently greater than 70% (see FIGS. 6A and 6B comparing mock and β-gal transfected primary chondrocytes). The dark blue clumps observed in FIG. 6B are a result of clumping of primary chondrocytes in culture. Relative levels of ONPG reaction, observed as difference in O.D. at 420 nm, confirm the observed differences in transfection efficiency (see FIG. 7).

Although the invention has been described with reference to the example provided above, it should be understood that various modifications can be made without departing from the spirit of the invention. Accordingly, the invention is limited only by the following claims.

I claim:

1. A composition for introducing an exogenous nucleic acid molecule into a permeabilized target cell, comprising:
   a) a synthetic liposome comprising an exogenous nucleic acid, at least one ligand, and a polymeric scaffold, wherein said polymeric scaffold is attached to both said ligand and said nucleic acid, and
   b) an in vitro or ex vivo target cell that has been permeabilized with an agent not comprising said liposome, wherein said agent is selected from the group consisting of lysolecithin, polyoxyethylenesorbitan monolaurate, octylphenoxy polyethoxy ethano, t-octylphenoxypolyethoxyethanol, phosphatidylcholine, and phospholipase.

2. The composition of claim 1, wherein said ligand can bind to a molecule expressed by said target cell.

3. The composition of claim 2, wherein said molecule expressed by said target cell comprises a cell surface receptor.

4. The composition of claim 1, wherein said liposome is selected from the group consisting of cationic liposomes, anionic liposomes, and synthetic lipid microspheres.

5. The composition of claim 1, wherein said ligand is transferrin.

6. The composition of claim 1, wherein said polymeric scaffold is selected from the group consisting of positively charged polymeric scaffolds, uncharged polymeric scaffolds, homopolymeric scaffolds, and poly-L-lysine scaffolds.

7. The composition of claim 1, wherein said target cell is a primary cell.

8. The composition of claim 1, wherein said target cell is a mammalian cell.

9. The composition of claim 8, wherein said mammalian cell is a human cell.

10. The composition of claim 8, wherein said mammalian cell is a perichondrial cell.

11. The composition of claim 1, wherein said nucleic acid is contained within a vector.

12. A method for high efficiency transfection comprising the steps of:
    a) providing:
       i) a plurality of synthetic liposomes comprising at least one ligand, a polymeric scaffold, and exogenous nucleic acid, wherein said polymeric scaffold is attached to both said ligand and said nucleic acid,
       ii) a plurality of in vitro or ex vivo perichondrial target cells, and
          iii) at least one permeabilization agent not comprising said liposome;
    b) exposing said plurality of target cells to said permeabilization agent to produce a plurality of permeabilized cells; and
    c) transfecting said permeabilized cells with said liposomes, under conditions such that said exogenous nucleic acid is introduced into said permeabilized cells, to produce a transfected cell, wherein transfection efficiency is at least 50%.

13. The method of claim 12, wherein said liposome is selected from the group consisting of cationic liposomes, anionic liposomes, and synthetic microspheres.

14. The method of claim 12, wherein said ligand is transferrin.

15. The method of claim 12, wherein said polymeric scaffold is selected from the group consisting of positively charged polymeric scaffolds, uncharged polymeric scaffolds, homopolymeric scaffolds, and poly-L-lysine scaffolds.

16. The method of claim 12, wherein said target cell is a primary cell.

17. The method of claim 12, wherein said target cell is a mammalian cell.

18. The method of claim 17, wherein said mammalian cell is a human cell.

19. The method of claim 12, wherein said nucleic acid is contained within a vector.

20. The method of claim 12, wherein said permeabilization agent is selected from the group consisting of lysolecithin, polyoxyethylenesorbitan monolaurate, octylphenoxy polyethoxy ethanol, t-octylphenoxypolyethoxyethanol, phosphatidylcholine, phospholipase, osmotic shock, and electric pulses.

21. The method of claim 12, wherein said ligand binds to a molecule expressed by said permeabilized cell.

22. The method of claim 12, wherein said molecule is a cell surface receptor.

23. The composition of claim 1, wherein said ligand is covalently attached to said polymeric scaffold.

24. The method of claim 12, wherein said ligand is covalently attached to said polymeric scaffold.

* * * * *